US005268178A

United States Patent [19]

Calhoun et al.

[11] Patent Number: 5,268,178

[45] Date of Patent: Dec. 7, 1993

[54] BIODEGRADABLE ANTIBIOTIC IMPLANTS AND METHODS OF THEIR USE IN TREATING AND PREVENTING INFECTIONS

[75] Inventors: Jason H. Calhoun; Jon T. Mader, both of Galveston, Tex.

[73] Assignee: The Board of Regents, The University of Texas System, Austin, Tex.

[21] Appl. No.: 881,886

[22] Filed: May 12, 1992

Related U.S. Application Data

[63] Continuation-in-part of Ser. No. 643,163, Jan. 18, 1991, abandoned, which is a continuation of Ser. No. 411,692, Sep. 25, 1989, abandoned.

[51] Int. Cl.$^5$ ............................................. A61F 2/00
[52] U.S. Cl. ..................................... 424/426; 424/422; 424/423; 424/428; 424/433
[58] Field of Search ............... 424/423, 426, 428, 422, 424/433

[56] References Cited

U.S. PATENT DOCUMENTS

| | | | |
|---|---|---|---|
| 3,773,919 | 11/1973 | Boswell | 424/19 |
| 3,867,190 | 2/1975 | Schmitt | 117/138.8 A |
| 3,882,858 | 5/1975 | Klemm | 128/92 G |
| 3,991,766 | 11/1976 | Schmitt | 424/22 |
| 4,107,121 | 8/1978 | Stoy | 260/29.6 |
| 4,159,322 | 6/1979 | Cloyd | 424/181 |
| 4,297,993 | 11/1981 | Harle | 128/92 D |
| 4,526,909 | 7/1985 | Urist | 523/115 |
| 4,587,268 | 5/1986 | Pfirrmann | 514/774 |
| 4,610,692 | 9/1986 | Eitenmuller | 623/16 |
| 4,612,337 | 9/1986 | Fox | 523/113 |
| 4,671,768 | 6/1987 | Ton | 433/174 |
| 4,740,382 | 4/1988 | Greco | 427/2 |
| 4,749,585 | 6/1988 | Greco | 427/2 |
| 4,772,203 | 9/1988 | Scheunemann | 433/173 |
| 4,997,904 | 3/1991 | Domb | 528/206 |
| 4,999,417 | 3/1991 | Domb | 528/271 |
| 5,100,669 | 3/1992 | Hyon et al. | 424/426 |

OTHER PUBLICATIONS

Calhoun, "Antibiotic Beads in the Management of Surgical Infections," American Journal of Surgery 157:443-449 (1989).

Calhoun, "Failure of Bipolar Hip Arthoplasty Secondary to Retained Antibiotic-Impregnated Polymethylmethacrylate Beads", Journal of Bone and Joint Surgery 8:1246-1248 (1988).

Calhoun, "Treatment of Osteomyelitis with a Biodegradable Antibiotic Implant: Studies with a Rabbit Model" (1990).

Calhoun, "Development of a Biodegradable Antibiotic Implant to Treat Osteomyelitis" (grant proposal Orthopedic Research Fund, Park Ridge, Ill., 1987).

Kitchell et al. "Poly(lactic/glycolic acid) Biodegradable Drug-Polymer Matrix Systems", Methods in Enzymology 112:436–447 (1985).

Tice et al. "Biodegradable Controlled-Release Parenteral Systems", Pharmaceutical Technology 26-34 (Nov. 1984).

(List continued on next page.)

Primary Examiner—Thurman K. Page
Assistant Examiner—James M. Spear
Attorney, Agent, or Firm—Arnold, White & Durkee

[57] ABSTRACT

Methods are disclosed for preventing or treating infection in a living patient at the site of a void in the patient's body created by surgery. The methods involve the use of biodegradable antibiotic implants which are placed in the surgical void and then supply an extended, continuous supply of at least one antibiotic to the surrounding tissue. The biodegradable implant comprises at least one biodegradable material such as polylactic acid, and at least one antibiotic drug. These components are combined and formed into bead, rods, or a gel which can be placed in the surgical void. The implant preferably comprises a plurality of antibiotics, each of which is specific to a different bacteria, which bacteria may be expected to be present at the site of the surgical void at different times after the void is created.

15 Claims, 9 Drawing Sheets

OTHER PUBLICATIONS

Chawla et al. "In-Vivo Degradation of Poly(Lactic Acid) of Different Molecular Weights", Biomat., Med. Dev., Art. Org., 13 (3 and 4), 153–162 (1985–1986).

Aoyagi et al., "Bioavailability of Griseofulvin from Tablets in Beagle Dogs and Correlation with Dissolution Rate and Bioavailability in Humans", Journal of Pharmaceutical Sciences 71:1169–1182 (Oct. 1982).

Khanna et al. "Bead Polymerization Technique for Sustained-Release Dosage Form", Journal of Pharmaceutical Science (May 1970).

Touitou et al. "New Hydrophilic Vehicle Enabling Rectal and Vaginal Absorption of Insulin etc.", J. Pharm. Pharmac. 30:662–663 (1978).

Kaetsu et al. "Controlled Slow Release of Chemotherapeutic Drugs for Cancer from Matrices Prepared by Radiation Polymerization at Low Temperatures", Journal of Biomedical Materials Research 14:185–197 (1980).

Bloomfield, et al., "Soluble Gentamicin Ophthalmic Inserts as a Drug Delivery System", Arch. Opthalmol. 96:885–887 (1978).

Calhoun, "Treatment of Diabetic Foot Infections: Wagner Classification, Therapy, and Outcome", Foot & Ankle 9:101–106 (1988).

Calhoun, "Biodegradable Antibiotic Implant for Bone Infections," (1989 NIH grant proposal).

BIODEGRADABLE ANTIBIOTIC IMPLANTS AND METHODS OF THEIR USE IN TREATING AND PREVENTING INFECTIONS

The United States Government has certain rights in the present invention pursuant to NIH Grant No. S07RR05427.

This application is a continuation-in-part U.S. Ser. No. 07/643,163, filed on Jan. 18, 1991, now abandoned which is a continuation of U.S. Ser. No. 07/411,692, filed on Sep. 25, 1989, now abandoned. Both of those applications are incorporated here by reference.

BACKGROUND OF THE INVENTION

This invention relates to methods of preventing and treating infections. More specifically, it relates to the use of biodegradable implants which contain an antibiotic and provide a sustained release of that antibiotic when they are implanted into surgical voids.

Virtually all surgical procedures create some type of void or dead space within the patient's body. This is particularly true in the case of surgery to remedy a localized infection. The area where the infection is focused, an area of relative tissue ischemia, must be debrided and filled in. Further, antibiotics must be administered to prevent recurrence of infection in the void.

One example is chronic bone infection (osteomyelitis). The standard therapy includes debridement and sequestrectomy of infected, dead bone, followed by several weeks of intravenous antibiotics. Unfortunately this treatment has several drawbacks. The multiple doses of antibiotics that are needed can become quite expensive. Also, the intravenous route of administration does not allow the antibiotic to be specifically directed to the location of the infection. Further, intravenous administration of antibiotics requires an operation for placement of a catheter, which can lead to serious complications.

One improvement to this procedure is the use of polymethylmethacrylate (PMMA) beads that contain antibiotics. Such beads are placed in surgical voids and thereby fill the voids, as well as providing local bactericidal levels of antibiotic. However, even these PMMA beads have disadvantages. First, they usually can only provide bactericidal levels of antibiotic for about two weeks, so parenteral antibiotic must be given also. Second, the PMMA beads must eventually be removed surgically, resulting in further trauma to the patient's body. Third, the beads provide no flexibility in the release rate of the antibiotic. This is important, because antibiotics are needed for longer periods to treat slow healing, ischemic wounds, such as in bone, than for more rapidly-healing, well vascularized wounds, such as in muscle.

Also, it is common for one type of bacteria to be present initially in a surgical void and, as treatment with a first antibiotic eliminates that organism, for a second type of bacteria to become present. Often, the second type of bacteria cannot be effectively treated with the same antibiotic as the first type of bacteria. Therefore, an implant that releases a single antibiotic, or releases multiple antibiotics at about the same rate, will not be fully effective in such a situation.

A long-standing need exists for improved methods for preventing and treating infections in voids created by surgery.

SUMMARY OF THE INVENTION

The present invention relates to a method of preventing or treating infection in a living patient at the site of a void in the patient's body created by surgery. The method comprises placing a biodegradable implant in the surgical void. The biodegradable implant comprises at least one biodegradable material selected from the group consisting of polymers of lactic acid, oligomers of lactic acid, polymers of glycolic acid, oligomers of glycolic acid, copolymers of lactic and glycolic acid, and mixtures thereof; at least one antibiotic drug which is specific for bacteria which are initially present at the site of the surgical void; and at least one other antibiotic drug which is specific for other bacteria which are not initially present in a substantial concentration at the site of the surgical void but will become present at the site of the surgical void in a substantial concentration at some time after the biodegradable implant is placed in the surgical void. "Specific" for a particular bacteria means that the antibiotic exhibits selective toxicity for that type of bacteria.

In one preferred embodiment, at least one antibiotic drug which is specific for bacteria that are initially present is substantially totally released from the biodegradable implant into the surrounding tissue within a period of about 2-4 weeks after the biodegradable implant is placed into the surgical void, and at least one other antibiotic drug which is specific for bacteria that will become present at a subsequent time is substantially totally released from the biodegradable implant into the surrounding tissue within a period of about 6-10 weeks after the biodegradable implant is placed into the surgical void.

In another aspect the invention relates to a method where at least one antibiotic drug which is specific for bacteria that are initially present is released from the biodegradable implant into the surrounding tissue at a substantially higher rate than at least one other antibiotic drug which is specific for bacteria that will become present at a subsequent time.

The weight ratio of biodegradable material to antibiotic drugs is preferably between about 50:1 and about 5:1, most preferably about 10:1. The higher the ratio, the faster the implant will dissolve, and the faster the antibiotic will elute.

In a particular embodiment, the antibiotic drugs clindamycin and vancomycin are used in a weight ratio of about 10:1. The clindamycin is substantially totally released from the biodegradable implant into the surrounding tissue within a period of about 2-4 weeks after the biodegradable implant is placed in to surgical void, and the vancomycin is substantially totally released from the implant within a period of about 6-10 weeks. In another particular embodiment, the antibiotic drugs used are tobramycin and clindamycin in a 10:1 weight ratio.

In another aspect of the invention, the method comprises placing an implant as specified above in a surgical void in a living patient, were the implant provides an effective antibacterial concentration of at least one antibiotic drug in the tissue surrounding the surgical void for a period of between about two week and six months after the implant is placed in the void. Where the implant is needed to treat cellulitis, the implant preferably provides an effective antibacterial concentration of at least one antibiotic drug in the tissue surrounding the surgical void for a period of about 2-4 weeks. In the case of osteomyelitis, the implant that is used after removal of necrotic tissue preferably provides an effective antibacterial concentration of at least one antibiotic drug in the tissue surrounding the surgical void for a period of about 6-10 weeks after the placement of the implant. And, if the purpose is long-term prophylaxis, the implant preferably provides a prophylactically effective antibacterial concentration of at least one antibiotic drug in the tissue surrounding the surgical void for a period of about 2-6 months.

The present invention also relates to biodegradable antibiotic implants for use in the above-described methods, and having the components and properties specified above.

The present invention has a number of advantages over previous treatments. For example, the present invention can provide bactericidal levels of antibiotics for the prolonged period of time necessary to treat a particular infection completely. This can vary, from 4-6 weeks for osteomyelitis or infected arthroplasty, to longer periods of time for prophylaxis, slow healing wounds such as diabetic osteomyelitis, or long term suppression of infection. In addition, the slow degradation of the implant allows the soft tissue left after degradation to slowly fill the void as the implant is absorbed. The need for surgical removal of the implant, as well as the need for parenteral antibiotics, is eliminated. Further, the biodegradable beads of the present invention are less expensive, have lower morbidity, and cause fewer complications, than prolonged parenteral antibiotics or PMMA beads.

In tests of treatment with biodegradable antibiotic beads in comparison to treatment with parenteral antibiotics alone, debridement alone, and debridement plus parenteral antibiotics, the present invention demonstrated a significant advantage. Compared to non-treatment controls, the use of parenteral antibiotics alone or debridement alone reduced bacterial infection by a factor of ten, while debridement plus biodegradable antibiotic beads or debridement plus parenteral antibiotics reduced the infection by a factor of 1,000 to 10,000.

Biodegradable antibiotic implants in accordance with the present invention can be used in treating established infections such as osteomyelitis, infected prostheses (plates, screws, joint arthroplasties), or soft tissue abscesses (intraperitoneal, bladder, chest, extremities, head, and neck). They can also be used to prevent these types of infections, and therefore can be applied in the treatment of open and closed fractures, reconstructive bone and joint surgery, and soft tissue surgery in the abdomen, pelvis, chest, extremities, head, and neck.

DETAILED DESCRIPTION OF SPECIFIC EMBODIMENTS

Figure 1:
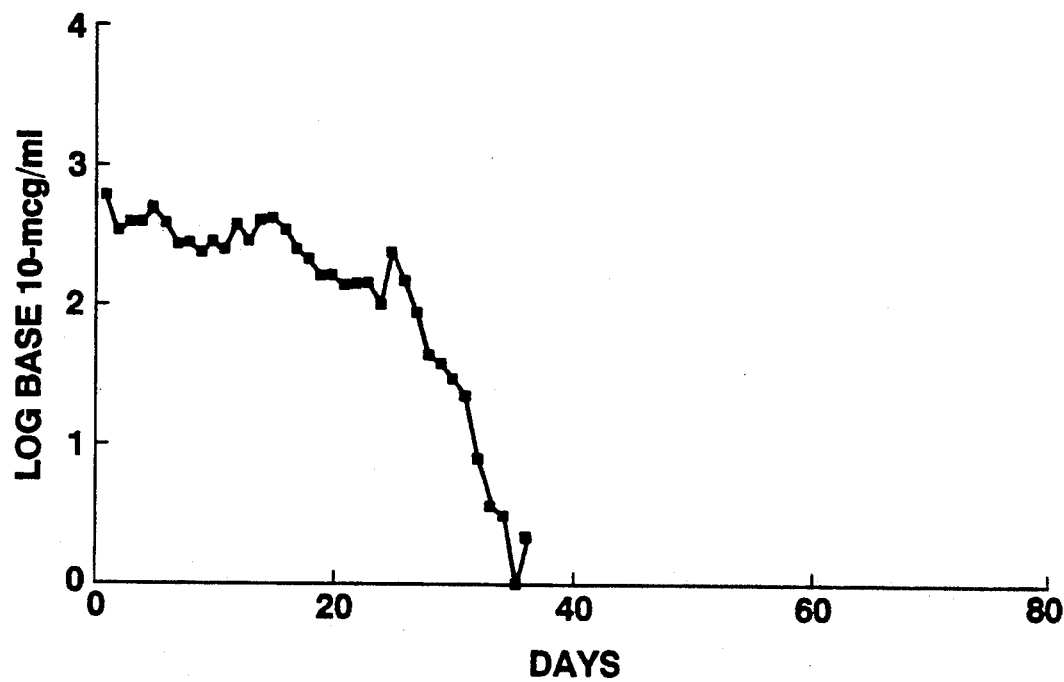
FIGS. 1-15 are elution graphs showing the concentration (micrograms/ml) of antibiotic generated in a solution in a test tube when a biodegradable bead in accordance with the present invention was placed in the solution.
Figure 2:
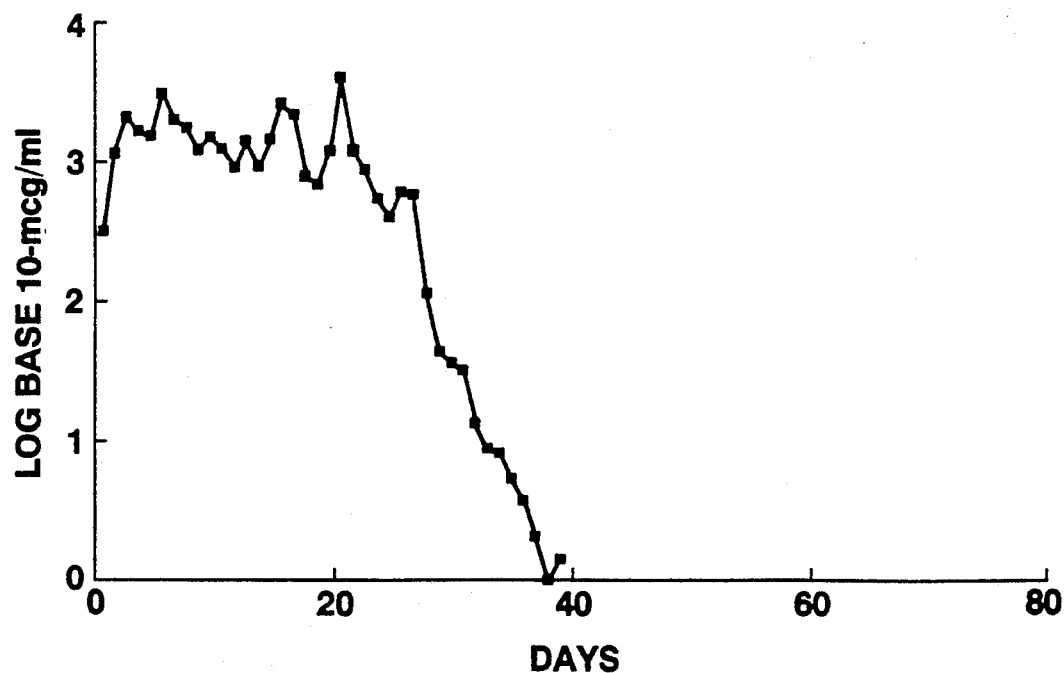
Figure 3:
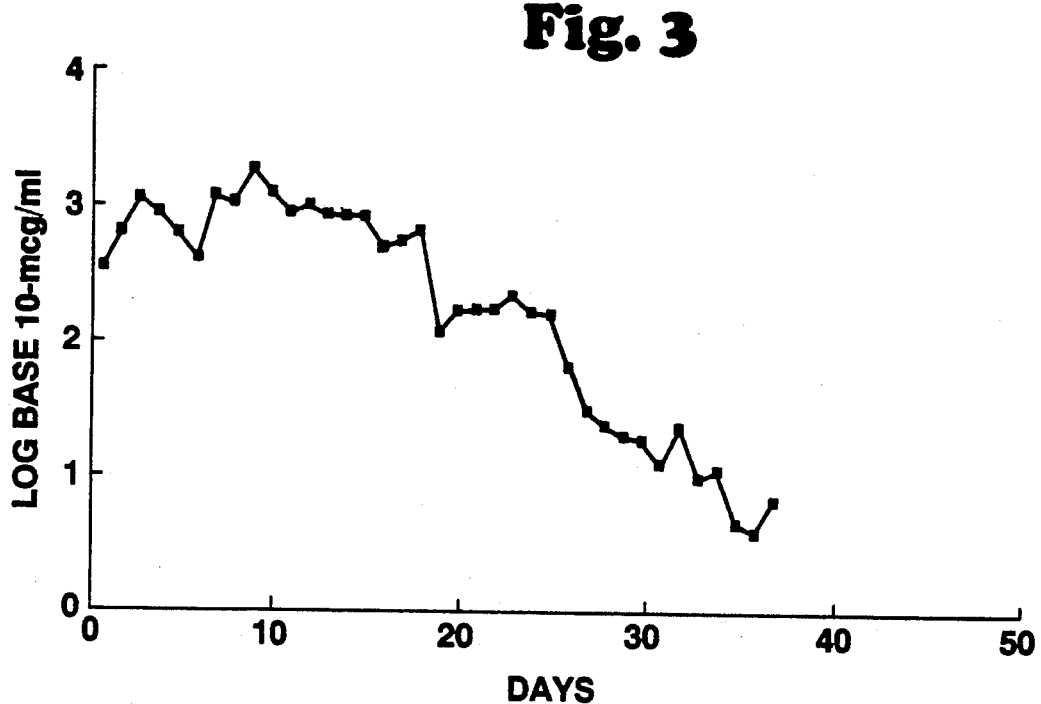
Figure 4:
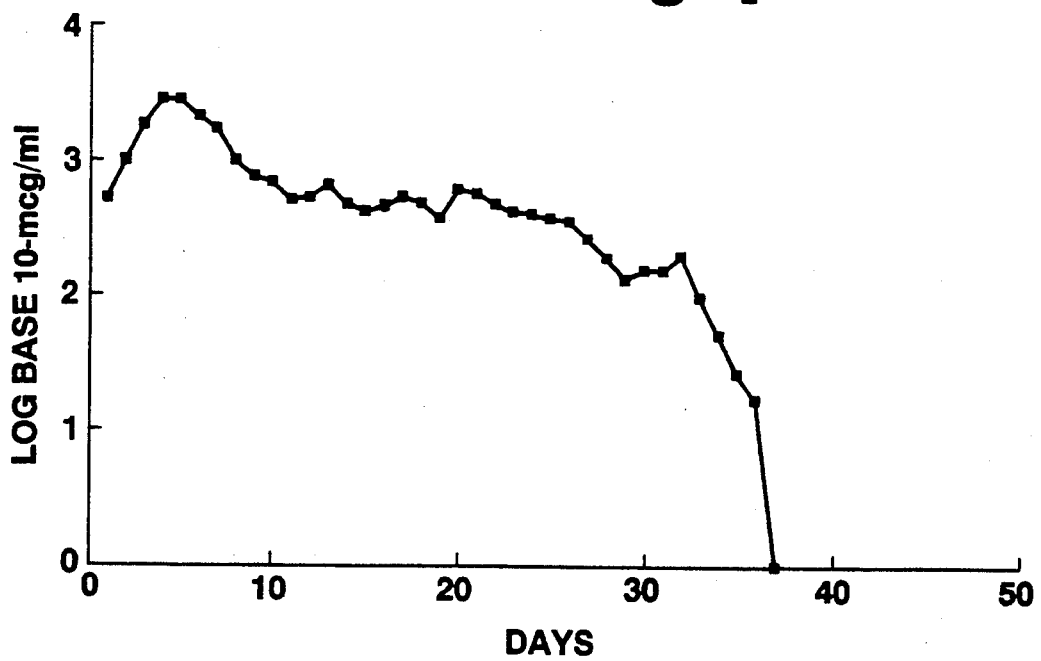
Figure 5:
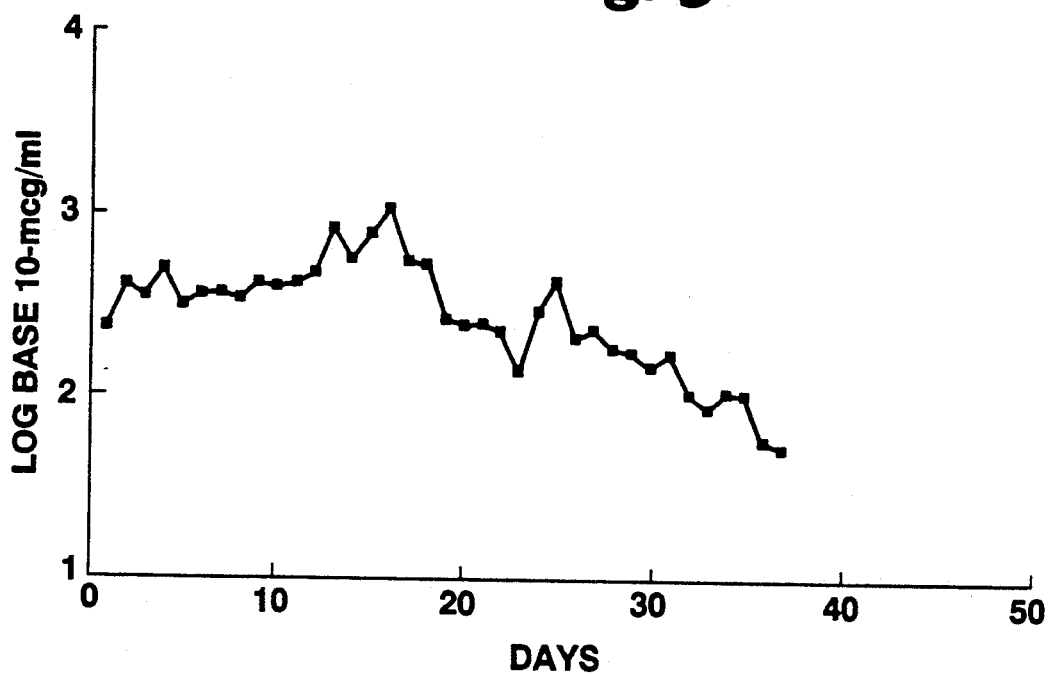
Figure 6:
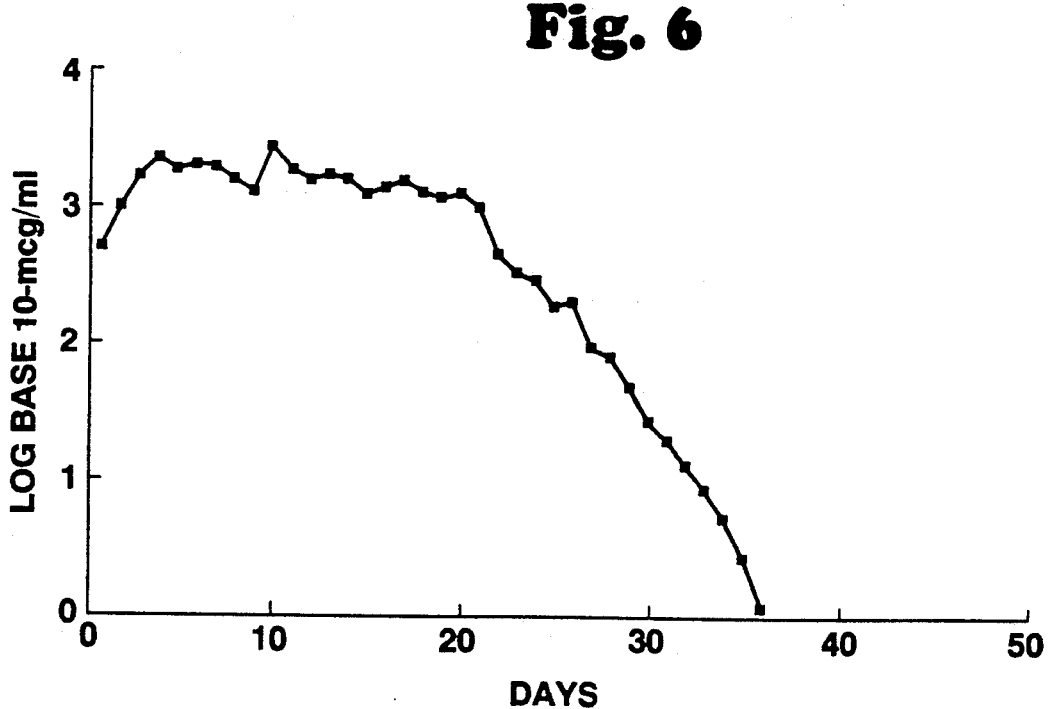
Figure 7:
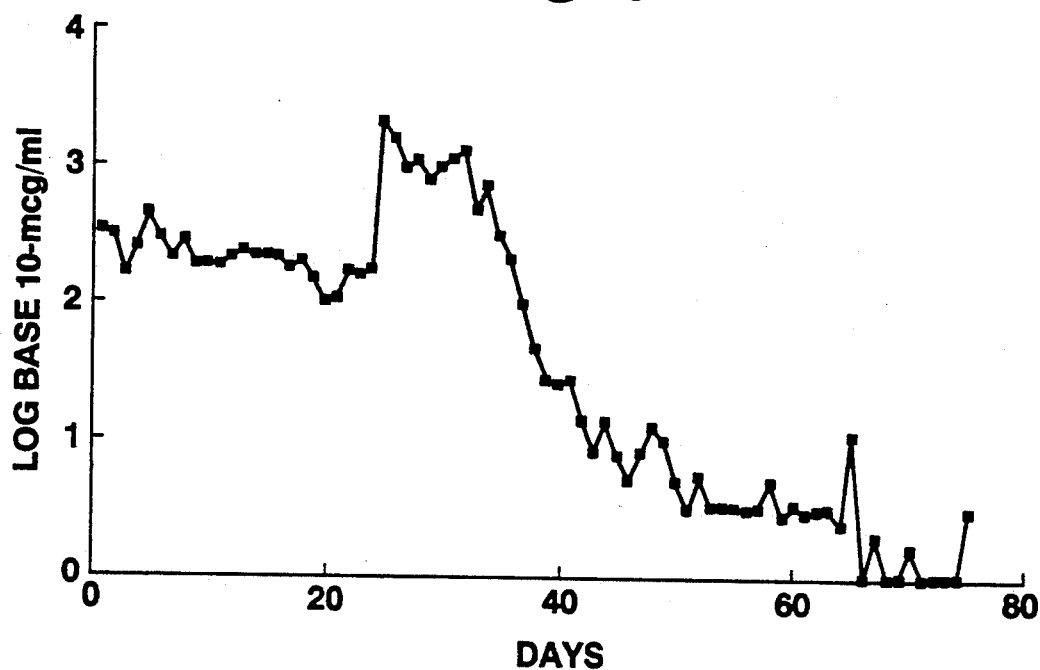
Figure 8:
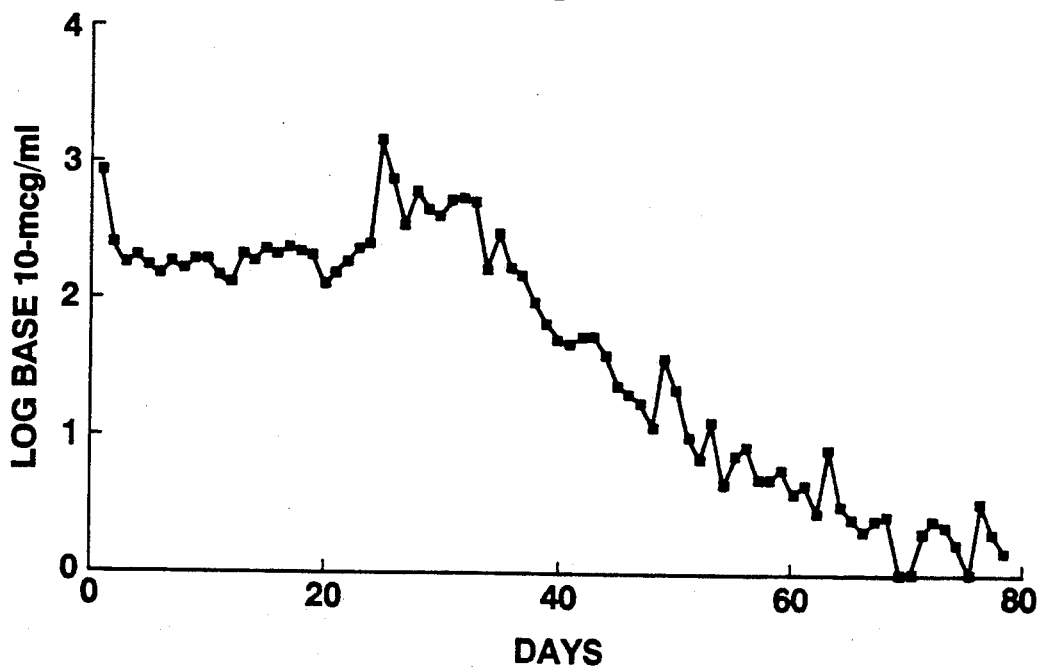
Figure 9:
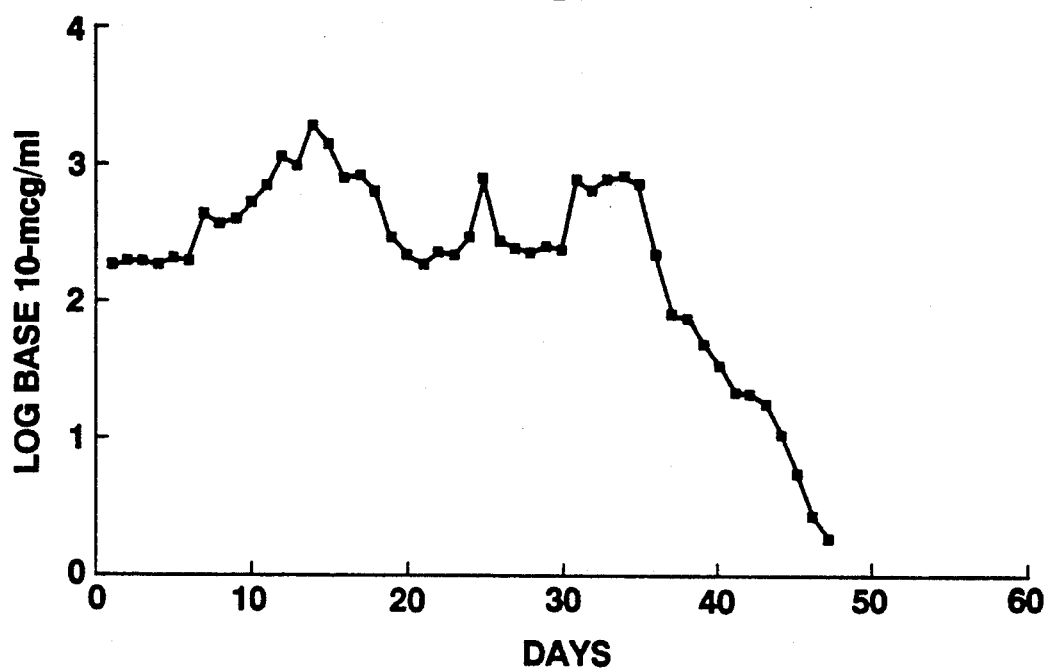
Figure 10:
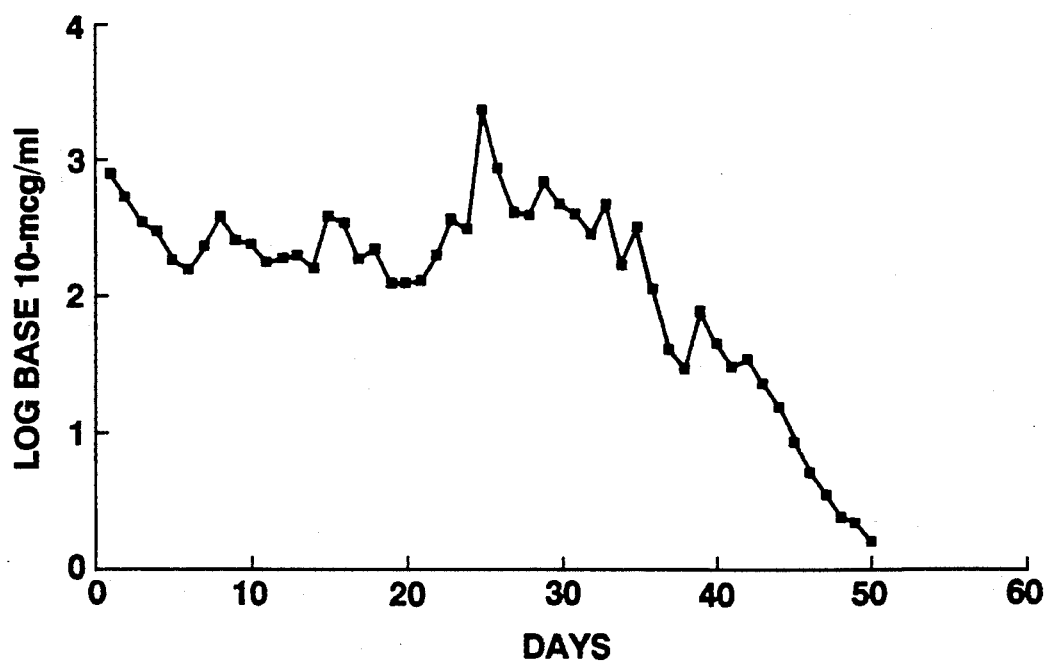
Figure 11:
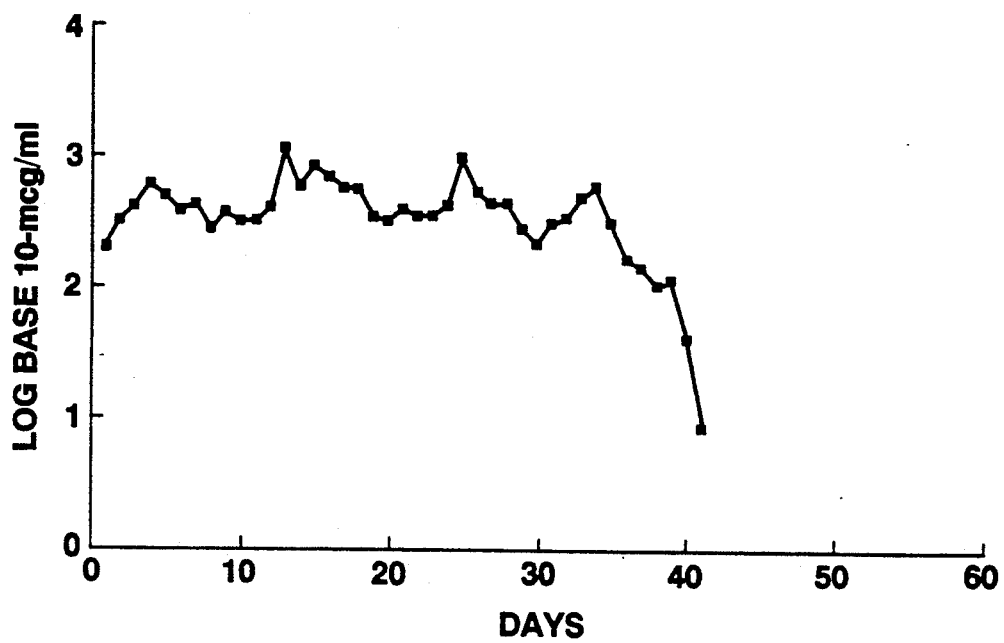
Figure 12:
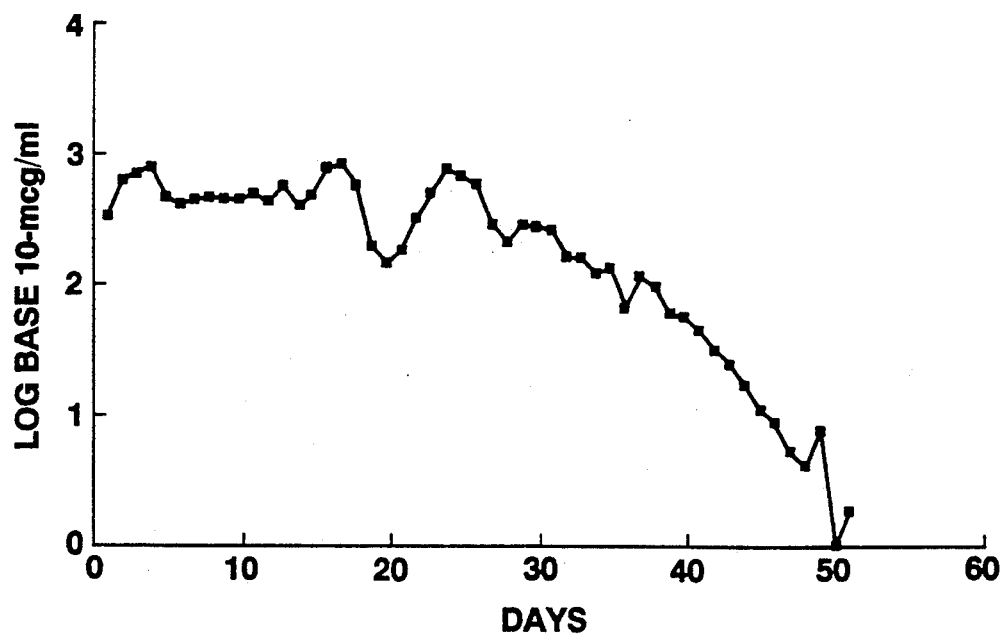
Figure 13:
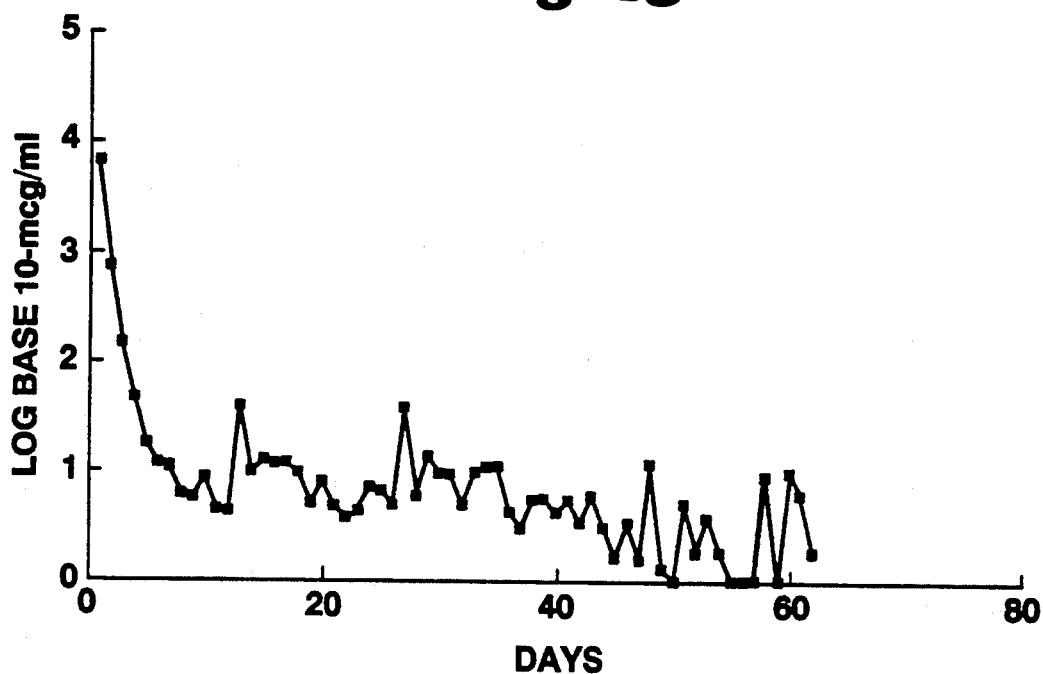
Figure 14:
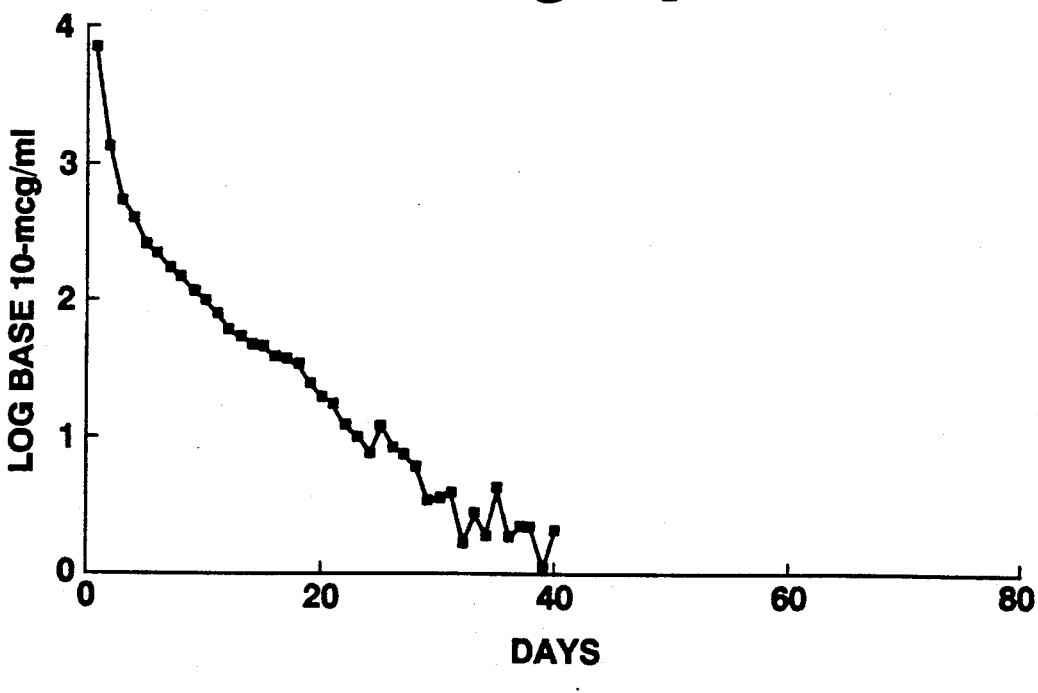
Figure 15:
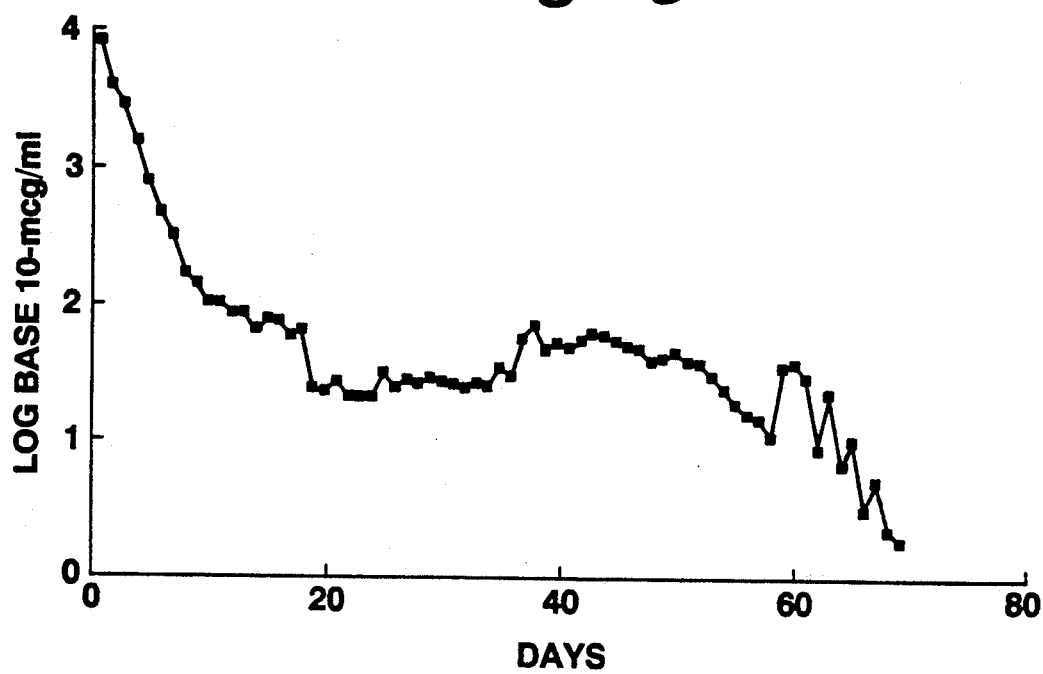

The present invention makes use of biodegradable materials that will be gradually dissolved in the body of a living subject, and which can be impregnated with an antibiotic drug, thereby resulting in the gradual release of the drug into the surrounding tissue of the subject's body. Suitable biodegradable materials will be readily dissolvable in vivo, and will not have any substantial toxic or other harmful effect on the subject. Examples of suitable biodegradable materials are polylactic acid, polyglycolic acid, dilactic acid, and lactic acid-glycolic acid copolymers. For instance, polyglycolic acids having molecular weights of 250, 50,000, and 80,000 daltons can be used. Also, dilactic acid/polyglycolic acid ratios of 75/25 and 85/15 by weight can be used. Such biodegradable materials can be purchased from Poly Sciences Incorporated, Moorington, Pa.

Variations in the composition, such as the molecular weight of each of the biodegradable materials and their relative proportions, affect the release rate of the antibiotic, and therefore allow the rate to be modified to meet the requirements of different treatment situations. In general, the lower the molecular weight of the biodegradable material, the faster it will dissolve. Suitable compositions in this regard include mixtures and copolymers of dilactic acid and polyglycolic acid, as beads made from such a combination will have a two-phase release curve. A first high release rate period occurs immediately after implant, A second one occurs about three to six weeks later. There is a sustained, lower release rate between the two peaks and after the second peak, until the bead is completely absorbed.

A variety of antibiotic drugs can be used in the implants to treat or prevent infection. Suitable antibiotics include many classes, such as aminoglycosides, penicillins, cephalosporins, semi-synthetic penicillins, and quinolines. Nafcillin, however, has been found not to have a desirable release rate from polylactic-polyglycolic acid beads. It is preferred that the drug used be specific for the bacteria present, and/or for other bacteria that are not initially present but that will become present at a subsequent time.

Certain antibiotics are released more efficiently from, for example, polylactic acid, but these antibiotics are not necessarily the best for treating all bacteria that may be present in or near a surgical void. The preferred antibiotic for use with polylactic acid in an implant to treat *Staphylococcus aureus* is clindamycin. After that bacteria is treated with clindamycin, it often mutates to methicillin-resistant or clindamycin-resistant strains. Vancomycin can suitably be used against the latter bacteria. Therefore, one preferred embodiment of the invention for use against *Staphylococcus aureus* is a combination of clindamycin and vancomycin in a single biodegradable implant, in a weight ratio of 10:1. Furthermore, the clindamycin should be released by the implant first at a relatively rapid rate, e.g., over about 2-4 weeks after the implant is placed into the surgical void. The vancomycin should preferably be released over a longer period at a relatively moderate rate, e.g., 6-10 weeks.

Such a clindamycin/vancomycin/polylactic acid implant will be effective against most Gram-positive bacteria, such as *Staphyloccus epidermis*, various Streptococcus species, anaerobic species, methicillin-resistant Staphylococci, Enterococci, and Clostridia. For Gram-negative bacteria, such as *Pseudomonas aeruginosa*, Acineobacter, *E. Coli*, Klebsiella, Enterobacteriaceae, Providencia, Proteus, and Serratia, the presently preferred implant is a 10:1 weight ratio of tobramycin and clindamycin, in polylactic acid. The tobramycin is effective against the Gram-negative bacteria and clindamycin is effective against the anaerobes and the Gram-positive organisms that frequently colonize or eventually infect Gram-negative wounds.

The weight ratio of biodegradable material to antibiotic is preferably between about 50:1 and about 5:1, and is most preferably about 10:1.

Other pharmaceutically acceptable drugs, additives, or excipients can also be included in the implant. The implant can take a number of suitable forms, such as approximately spherical pellets or beads (preferably having a diameter between 2–9 mm), rods, or a gel.

One procedure for making the implants is to obtain a biodegradable material, such as polylactic acid, in the form of a powder, and dissolve it in acetone. The antibiotic is added in the desired proportion, and then the mixture is dried to form a thin layer. These steps are repeated, forming a multiple layer, sandwich-like material. The material can then be cut or rolled into the desired shape, such as cylinders, spherical beads, or pellets of other shapes. The pellet is preferably then sealed by dipping it in acetone and drying it until it is hard. It is also desirable to sterilize the implant with electron beam or gamma radiation before placing it in the wound or void.

Figure 17:
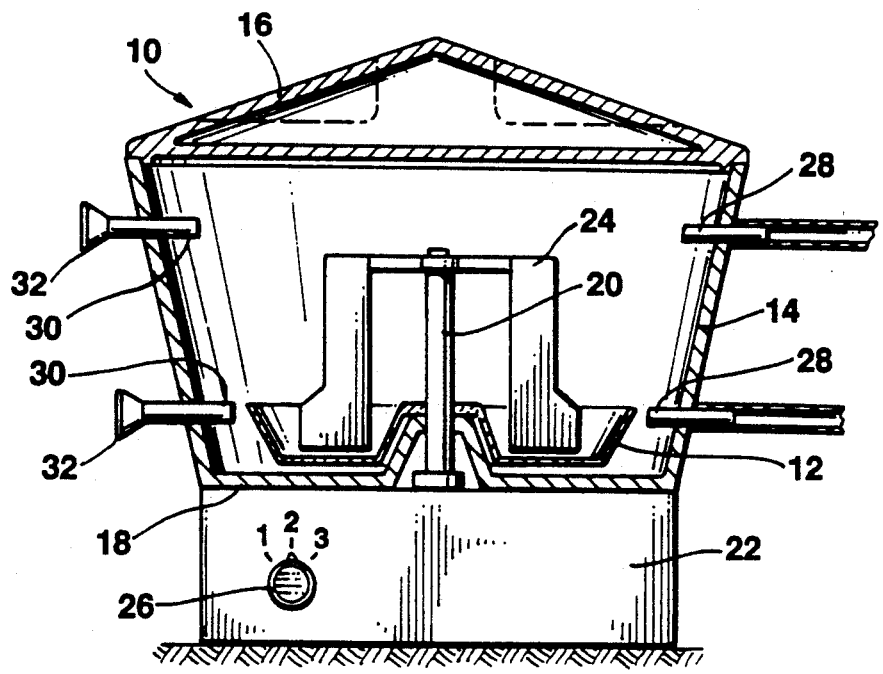
FIG. 17 shows a cross-sectional side view of a mixing apparatus for preparing biodegradable antibiotic implants in accordance with the present invention.

It is advantageous to be able to manufacture the implant in an operating room suite, in order to minimize storage problems. In order to achieve this, a mixing and blending apparatus as shown in FIG. 17 can be used. After the biodegradable material, such as a polylactic acid powder, is sterilized, for example by means of gamma radiation, it is placed in the blending apparatus 10 in an internal reservoir 12. The apparatus includes a side enclosure member 14, a cap member 16, and a base enclosure member 18. Extending upward through the base enclosure member 18 and the reservoir 12 is a rotatable shaft 20. The shaft 20 is driven by an electric motor (not shown) which is located in a base unit 22. Attached to the shaft 20 are mixing blades 24, which rotate along with the shaft. The motor preferably operates at a plurality of speeds, which can be selected by means of a switch 26 on the base unit 22.

Methylene chloride is combined with the polylactic acid in the reservoir 12. The desired antibiotics are added. A vacuum is then applied by attaching hoses from a vacuum pump (not shown) to outlets 28 in the side enclosure member 14. A vacuum of 60 psi negative is preferably applied for 45 minutes. At the same time, external air is permitted to enter the apparatus 10 through inlet openings 30 in the side enclosure member 14, each of which has an air filter 32 to remove contaminants. The effect is to cause a flow of air across the interior of the blending apparatus while the components are being blended, which aids in the removal of the methylene chloride. It is preferred to rotate the mixing blades for at least 45 minutes, at a speed of between about 60–200 rpm.

It has been found that variations in the speed of the mixing blades will affect the biodegradation of the resulting product. As the blending speed is increased, the blending incorporates increasing amounts of air into the blend, which will tend to increase the speed of biodegradation of the implant. The ambient humidity and the strength of the vacuum used will also affect the rate of biodegradation of the end product.

The mixed polylactic acid and antibiotics collect on the blades 24 as the drying continues. After the rotation of the blades is stopped, the mixed material can be removed from the blades and formed into beads, rods, or a gel. The greater the amount of air incorporated the more the consistency of the material tends toward a gel rather than a solid bead.

The implant can be placed in a surgical void before the void is sealed with sutures. Preferable, the amount of the implant used will completely fill the void.

Biodegradable antibiotic beads in accordance with the present invention were tested in vitro by placing the beads into a test tube containing water and denatured buffer and measuring the concentration of antibiotic in the water over time, to determine the rate of antibiotic elution from the bead. Beads were prepared and tested having a variety of compositions in terms of biodegradable material, and containing either tobramycin, clindamycin, or vancomycin as the antibiotic drugs (10:1 weight ratio of biodegradable material to antibiotic in each instance). FIGS. 1–15 show the elution curves for these tests. The specific materials tested are summarized in Table 1 below:

TABLE 1

| FIGURE | ANTIBIOTIC | BIODEGRADABLE MATERIAL(S) |
|---|---|---|
| 1 | tobramycin | 70:30 PLCG |
| 2 | tobramycin | 70:30 PLCG/2000 PLA |
| 3 | clindamycin | 70:30 PLCG |
| 4 | clindamycin | 70:30 PLCG/2000 PLA |
| 5 | vancomycin | 70:30 PLCG |
| 6 | vancomycin | 70:30 PLCG/2000 PLA |
| 7 | tobramycin | 80:20 PLCG |
| 8 | tobramycin | 90:10 PLCG |
| 9 | clindamycin | 80:20 PLCG |
| 10 | clindamycin | 90:10 PLCG |
| 11 | vancomycin | 80:20 PLCG |
| 12 | vancomycin | 90:10 PLCG |
| 13 | tobramycin | 2000 PLA |
| 14 | clindamycin | 2000 PLA |
| 15 | vancomycin | 2000 PLA |

("70:30 PLCG" = copolymer of dilactic acid and polyglycolic acid, 70% lactide, 30% co-glycolide; "80:20 PLCG" = 80% lactide, 30% co-glycolide, etc., "2000 PLA" = 2000 m.w. polylactic acid.)

Table 2 below summarizes the results.

TABLE 2

| Biodegradable Material Type | Release and Dissolution Time (Day) for Implants | | | | | | | | |
|---|---|---|---|---|---|---|---|---|---|
| | Tobramycin | | | Clindamycin | | | Vancomycin | | |
| | High | Mod. | Low | High | Mod. | Low | High | Mod. | Low |
| 70:30 | 21 | 33 | 36 | 26 | NL | 37+ | 33 | NL | 37+ |
| 70:30/2000 | 28 | 36 | 39 | 33 | 37 | 37+ | 27 | 34 | 36+ |
| 80:20 | 37 | 51 | 75+ | 37 | NL | 47+ | 40 | NL | 41+ |
| 90:10 | 38 | 60 | 78+ | 37 | NL | 50+ | 36 | 48 | 51+ |
| 2000 | 4 | 42 | 62+ | 10 | NL | 40+ | 12 | 66 | 69+ |

(High, Mod. and Low refer to high, moderate, and low concentrations of antibiotic in the solution in the test tubes;
High = when antibiotic concentration becomes <100 micrograms (mcg)/ml;
Mod. = when antibiotic concentration becomes < breakpoint sensitivity, i.e., the target bacteria are no longer killed;
Low = when implant fully dissolves (low concentration of antibiotic until dissolution);
NL = concentration not lower than breakpoint sensitivity.)

In the treatment of cellulitis or soft tissue infection in lacerations, open fractures, surgical wounds, or joint infections, a high concentration of antibiotic and rapid biodegradation (2-4 weeks) are needed. The 70:30 and 70:30/2000 compositions met these criteria. (See FIGS. 1-6.) In osteomyelitis treatment, a moderate concentration of antibiotic and a moderate rate of biodegradation (6-10 weeks) are needed. The 80:20, 90:10, and 2000 compositions met these criteria. (See FIGS. 7-16.) For long-term suppression or prophylaxis, such as in diabetes mellitus, ischemic tissue, total joint arthroplasty, or internal fixation patients with peri-operative antibiotics and long term (i.e., months or years) antibiotic treatments, a low concentration and a slow rate of biodegradation (2-6 months) are needed. The 80:20 (tobramycin), 90:10 (tobramycin), and 2000 (tobramycin and vancomycin) compositions appeared most suitable for this purpose out of the ones tested. (See FIGS. 7, 8, 13, and 15.)

The invention was also tested in vivo in rabbits. A model of local osteomyelitis was developed in mature (18 weeks) New Zealand while rabbits. Localized osteomyelitis was produced by open implantation of $10^4$ Staphylococcus aureus organisms into a ⅛ inch drill hole in the proximal tibia. The drill hole was then one-third filled with ground autoclaved bone and capped with polymethylmethacrylate. Osteomyelitis developed over a three to four week period, and its presence was confirmed by X-ray.

Fifty-five such rabbits with localized proximal tibial osteomyelitis were separated into five study groups. The groups received the following treatments: (1) no treatment for the control group, (2) debridement surgery without antibiotics, (3) intramuscular vancomycin with no surgery, (4) debridement surgery plus implant of biodegradable beads in accordance with the present invention (no parenteral antibiotics), and (5) debridement surgery plus intramuscular vancomycin. The beads used for group four contained a 3:1 ratio of polylactic acid and dilactic acid, plus 10% vancomycin. In other words, the composition was approximately 67.5% by weight polylactic acid, 22.5% dilactic acid, and 10% vancomycin.

Figure 16:
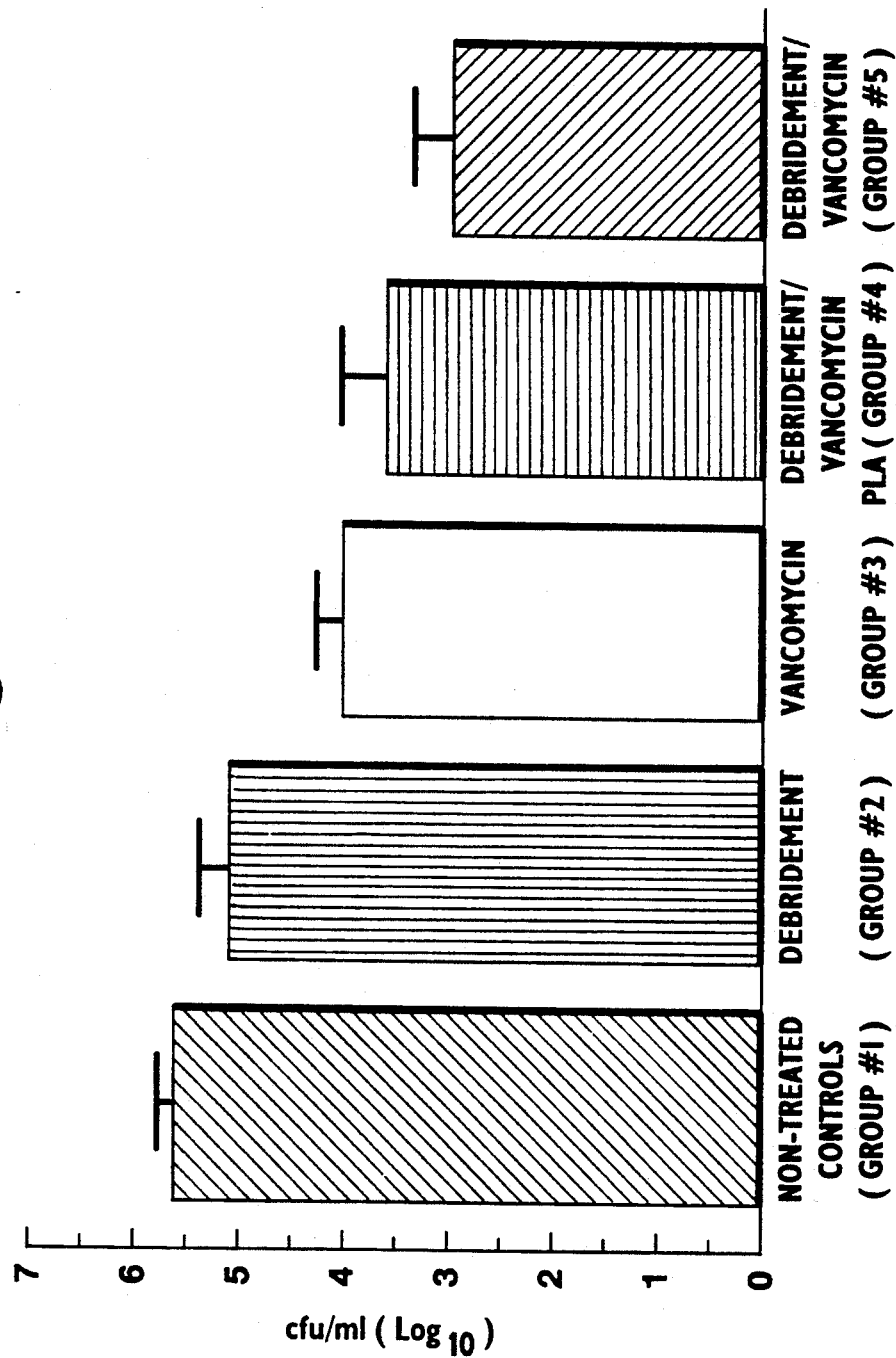
FIG. 16 is a graph of quantitative bacterial count (in colony forming units/ml) in a control group and four treatment groups of rabbits suffering from osteomyelitis.

As shown in FIG. 16, the control group had a significantly greater bacterial culture count than did the groups treated with debridement only or vancomycin only. The group treated with biodegradable antibiotic beads had a quantitative bacterial count (colony forming units) 2.1 logs better than the control group. The group treated with debridement plus intramuscular vancomycin had a slightly lower bacterial count than the group treated with the beads. The biodegradable beads were found to be only partially dissolved at the time of animal sacrifice, four weeks after the implant.

The preceding description is intended to illustrate specific embodiments of the present invention. It is not intended to be an exhaustive list of all possible embodiments. Persons skilled in this field will recognize that modifications could be made to the described embodiments which would remain within the scope of the invention.

We claim:

1. A method of preventing or treating infection in a living patient at the site of a void in the patient's body created by surgery, comprising placing in a surgical void in a living patient a biodegradable implant, the implant comprising:
   at least one biodegradable material selected from the group consisting of polymers of lactic acid, oligomers of lactic acid, polymers of glycolic acid, oligomers of glycolic acid, copolymers of lactic and glycolic acid, and mixtures thereof; and
   a first antibiotic drug which is specific to treat or prevent infection from bacteria which are initially present at the site of the surgical void, and a second antibiotic drug which is specific to treat of prevent infection from bacteria which are not initially present as a bacterial population effective to cause infection at the site of the surgical void but will become present as a bacterial population effective to cause infection at the site of the surgical void at some time after the biodegradable implant is placed in the surgical void;
   whereby the implant provides a two-phase antibiotic elution rate, in which the first antibiotic drug is released from the implant at a higher rate than the second antibiotic drug when the implant is first placed in the surgical void, and at a subsequent time the second antibiotic drug is released from the implant at a higher rate than the first antibiotic drug.

2. The method of claim 1, where the first antibiotic drug is substantially totally released from the biodegradable implant into the surrounding tissue within a period of about 2-4 weeks after the biodegradable implant is placed into the surgical void, and where the second antibiotic drug is substantially totally released from the biodegradable implant into the surrounding tissue within a period of about 6-10 weeks after the biodegradable implant is placed into the surgical void.

3. A method of preventing or treating infection in a living patient at the site of a void in the patient's body created by surgery, comprising placing in a surgical void in a living patient a biodegradable implant, the implant comprising:
   biodegradable lactic acid polymers; and
   the antibiotic drugs clindamycin and vancomycin;
   where the weight ratio of lactic acid polymers to the antibiotic drugs is about 10:1 and the weight ratio of clindamycin to vancomycin is about 10:1, where the clindamycin is substantially totally released from the biodegradable implant into the surrounding tissue within a period of about 2-4 weeks after the biodegradable implant is placed into the surgical void, and where the vancomycin is substantially totally released from the biodegradable implant into the surrounding tissue within a period of about 6-10 weeks after the biodegradable implant is placed into the surgical void.

4. The method of claim 1, where the weight ratio of biodegradable material to antibiotic drugs is between about 50:1 and about 5:1.

5. The method of claim 1, where the weight ratio of biodegradable material to antibiotic drugs is about 10:1.

6. The method of claim 1, where the biodegradable implant comprises the antibiotic drugs clindamycin and vancomycin.

7. The method of claim 6, where the weight ratio of clindamycin to vancomycin is about 10:1.

8. The method of claim 7, where the clindamycin is substantially totally released from the biodegradable implant into the surrounding tissue within a period of about 2-4 weeks after the biodegradable implant is placed into the surgical void.

9. The method of claim 6, where the vancomycin is substantially totally released from the biodegradable implant into the surrounding tissue within a period of about 6-10 weeks after the biodegradable implant is placed into the surgical void.

10. The method of claim 1, where the biodegradable implant comprises the antibiotic drugs tobramycin and clindamycin.

11. The method of claim 10, where the weight ratio of tobramycin to clindamycin is about 10:1.

12. A method of preventing or treating infection in a living patient at the site of a void in the patient's body created by surgery, comprising placing in a surgical void in a living patient a biodegradable implant, the implant comprising:
    at least one biodegradable material selected from the group consisting of polymers of lactic acid, oligomers of lactic acid, polymers of glycolic acid, oligomers of glycolic acid, copolymers of lactic and glycolic acid, and mixtures thereof; and
    a combination of antibiotic drugs selected from the group consisting of (a) clindamycin and vancomycin in a weight ratio of about 10:1, and (b) tobramycin and clindamycin in a weight ratio of about 10:1;
    where the weight ratio of the biodegradable material to the combination of antibiotic drugs is between about 50:1 and about 5:1.

13. A biodegradable implant for preventing or treating infection in a living patient at the site of a void in the patient's body created by surgery, comprising:
    at least one biodegradable material selected from the group consisting of polymers of lactic acid, oligomers of lactic acid, polymers of glycolic acid, oligomers of glycolic acid, copolymers of lactic and glycolic acid, and mixtures thereof; and
    a combination of antibiotic drugs selected from the group consisting of (a) clindamycin and vancomycin in a weight ratio of about 10:1, and (b) tobramycin and clindamycin in a weight ratio of about 10:1;
    where the weight ratio of the biodegradable material to the combination of antibiotic drugs in between about 50:1 and about 5:1.

14. The biodegradable implant of claim 13, where the weight ratio of biodegradable material to antibiotic drugs is about 10:1.

15. A biodegradable implant for preventing or treating infection in a living patient at the site of a void in the patient's body created by surgery, comprising:
    biodegradable lactic acid polymers; and
    the antibiotic drugs clindamycin and vancomycin;
    where the weight ratio of lactic acid polymers to the antibiotic drugs is about 10:1 and the weight ratio of clindamycin to vancomycin is about 10:1.

* * * * *

UNITED STATES PATENT AND TRADEMARK OFFICE
CERTIFICATE OF CORRECTION

PATENT NO. : 5,268,178

DATED : December 7, 1993

INVENTOR(S) : Calhoun et al.

It is certified that error appears in the above-identified patent and that said Letters Patent is hereby corrected as shown below:

In Claim 1, at column 8, line 6, "of" should be --or--.

Signed and Sealed this

Thirty-first Day of May, 1994

Attest:

BRUCE LEHMAN

*Attesting Officer*  *Commissioner of Patents and Trademarks*